United States Patent [19]
Sommer

[11] Patent Number: 5,939,727
[45] Date of Patent: Aug. 17, 1999

[54] CONTAMINATION SENSOR

[75] Inventor: Holger T. Sommer, Merlin, Oreg.

[73] Assignee: Caterpillar Inc., Peoria, Ill.

[21] Appl. No.: 08/996,044

[22] Filed: Dec. 22, 1997

[51] Int. Cl.[6] ................................. G01N 21/49
[52] U.S. Cl. .................. 250/573; 356/338; 356/340; 356/343; 356/442
[58] Field of Search .................... 250/573, 574, 250/564; 340/627, 630; 356/335, 336, 338, 339, 340, 341, 342, 343, 436, 437, 438, 439, 440, 441, 442

[56] References Cited

U.S. PATENT DOCUMENTS

| 4,260,258 | 4/1981 | Rose et al. ............................. | 356/335 |
| 4,917,496 | 4/1990 | Sommer ................................ | 356/336 |
| 4,934,183 | 6/1990 | Sommer et al. ....................... | 73/118.1 |
| 5,033,851 | 7/1991 | Sommer ................................ | 356/358 |
| 5,646,597 | 7/1997 | Hamburger et al. .................. | 340/627 |

OTHER PUBLICATIONS

Condition monitoring of fluid systems—the complete approach—M.J. Day; Insight, vol. 39, No. 8, Aug. 1977.

Primary Examiner—Edward P. Westin
Assistant Examiner—Thanh X. Luu
Attorney, Agent, or Firm—J.W. Burrows; Kevin M. Kercher

[57] ABSTRACT

A contamination sensor is provided for use in a fluid system and machinery to continuously monitor the level of contaminants in a fluid. The contamination sensor includes a source of light that is directed into the fluid stream with three photodetector arrangements detecting light scattered by contaminants contained in the fluid. The first photodetector arrangement is located near the origin of the source of light. The second photodetector arrangement is located farther away from the source of light. The third photodetector arrangement is located perpendicular to the axis of the light beam and spaced from the source of light along the axis of the light beam. The simultaneous detected scattered light from a contaminant in the fluid is converted to electrical signals by the photodetectors, conditioned by a signal conditioning circuit and transferred to a signal processing unit for interpretation. The subject contamination sensor provides an advanced but economical arrangement to effectively detect and identify contaminants in a fluid by type and quantity.

14 Claims, 2 Drawing Sheets

CONTAMINATION SENSOR

TECHNICAL FIELD

This invention relates generally to a sensor for detecting contaminants in oil or other types of fluids and more particularly to the construction of a contamination sensor that can be used in lubricants, fuels and power fluid systems during their normal use in machinery and mechanical systems.

BACKGROUND ART

There has been various efforts in the past to develop contamination sensors that can be mounted on machinery and in fluid power systems to continuously monitor contaminants in hydraulic fluids, fuels or lubricants. Some of these known designs use the concept of light extinction. This concept is related to the concept of light scattering. A beam of light is directed through the fluid and its intensity is monitored by a photodetector, located on the other side of the flow channel. The amount of light that gets through the fluid is measured and compared to the amount that was originally delivered from the source. The difference between the originally delivered light energy and the energy measured on the other side of the flow channel is the amount of light energy extinct. This amount of light energy is either absorbed by the fluid, absorbed by the contamination or scattered by contaminants in the fluid. The amount of light extinct is a measurement of the level (type, size and amount) of contaminants in the fluid. In various systems using light extinction, the light is directed through the fluid and by the use of a mirror the light is reflected back through the fluid to the photodetector. Other known designs use the concept of light scattering. This concept is also based on directing a beam of light through a fluid. However, light scattering sensors use the amount of light scattered as indication for the level of contaminants in the fluid. Detection of foreign matter (contaminants) in liquids through the light extinction or the light scattering concept are related. An energy balance reveals that the light energy extinct in a beam is composed out of all the light energy scattered in all directions (except into the direction of the light beam monitoring photo detector), the amount of light absorbed by the fluid (for a constant flow channel dimension this is a constant) and the amount of light energy absorbed by the contamination in the light beam. The contaminants might be solid particles, like sand or metal particles; droplets of immiscible fluids in the background fluid, like water droplets in oil or gas bubbles in the background fluid; and/or like air bubbles in a foaming lubricant. The photodetectors converts the light signals into electrical signals in response to the scattered light or the extinct light. The signals are in the form of light burst which are converted into electric pulses by the photodetector. The height of the pulses is a measurement of particle (droplet, bubble) size. Currently existing contamination sensors are too expensive to be placed in machines and/or fluid power system for reliable detection of different types and levels of contaminants; such as, solid particles, water droplets and air/gas bubbles.

The present invention is directed to overcoming one or more of the problems as set forth above.

DISCLOSURE OF THE INVENTION

In one aspect of the present invention, a contamination sensor is provided and adapted for use in a fluid system to continuously monitor the level of contaminants in the fluid. The contamination sensor includes a housing having first and second end portions. A source of light is disposed in the first end portion and operative to generate a light beam therefrom. First and second photodetector arrangements are disposed in the first end portion. The first photodetector is located near the source of light and the second photodetector arrangement is located at a distance away from the source of light farther than the first photodetector arrangement. A third photodetector arrangement is disposed in the first end portion and located perpendicular to the light beam generated by the source of light. A signal conditioning circuit is disposed in the second end portion and operative to generate conditioned signals representative of the light intensity sensed by the respective first, second, and third photodetector arrangements.

BEST MODE FOR CARRYING OUT THE INVENTION

Figure 1:
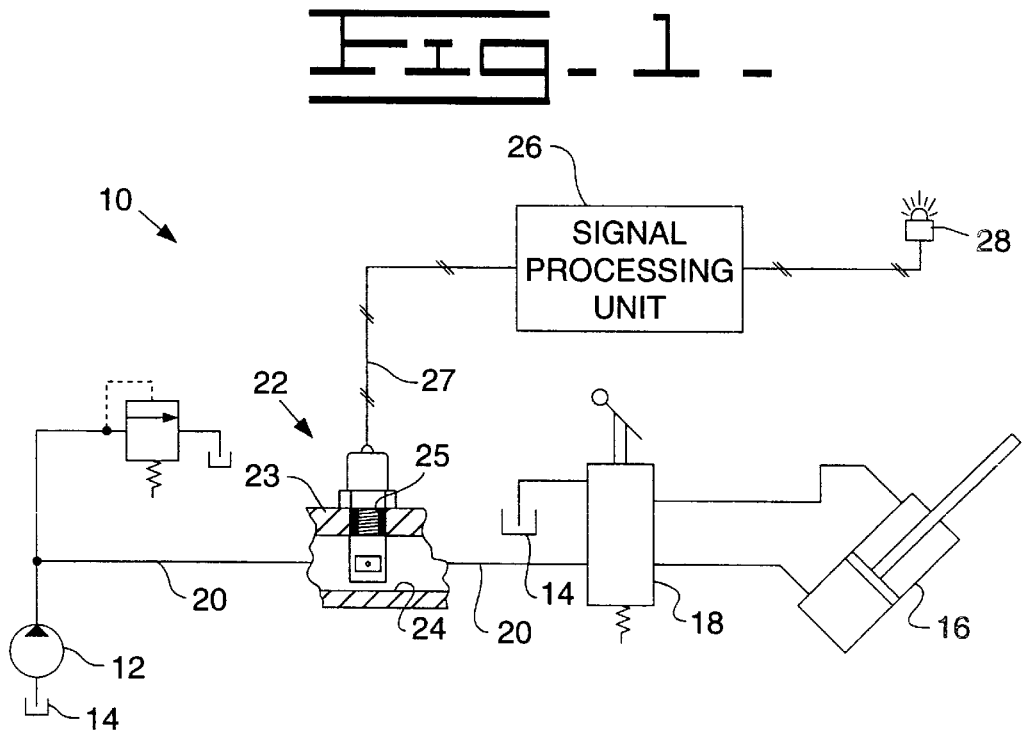
FIG. 1 is a partial diagrammatic and partial schematic representation of a fluid system incorporating the subject invention.

Referring to the drawings and more particularly to FIG. 1, a fluid system 10 is illustrated and includes a source of pressurized fluid, such as a hydraulic pump 12 that receives fluid, such as hydraulic oil, from a reservoir 14, an actuator 16 and a control valve 18 disposed in a supply conduit 20 between the pump 12 the actuator 16. The fluid system 10 also includes a contamination sensor 22 disposed the supply conduit 20 between the pump 12 and the control valve 18. In the subject embodiment, the contamination sensor 22 is connected to a sensor manifold 23. It is recognized that the contamination sensor 22 could be installed at other locations within the fluid system 10 or placed in a parallel shunt line (not shown) without departing from the essence of the subject invention. Likewise, it is recognized that the sensor manifold 23 could be of various configurations. In the subject embodiment, the sensor manifold 23 is disposed in the supply conduit 20 and has a passage 24 defined therein with a threaded hole 25 defined perpendicular thereto.

A signal processing unit 26 is connected to the contamination sensor 22 by an electrical line 27 and operative to receive signals from the contamination sensor 22 that is representative of the level and type of contamination in the fluid of the fluid system 10. An indicator lamp, such as a bulb or light emitting diode 28, is connected to the signal processing unit 26 and will be illuminated in the event the contamination within the fluid of the fluid system 10 exceeds a predetermined level or composition. It is also recognized that the information from the signal processing unit 26 could be sent to a monitoring or control unit for other desired uses. As an example, a system could be shut down to prevent catastrophic failure of the equipment or to indicate a need for service. Also by detecting the type of contamination and knowing when the contamination occurred during machine operation, preventive maintenance is pinpointed to specific parts of the system.

Figure 2:
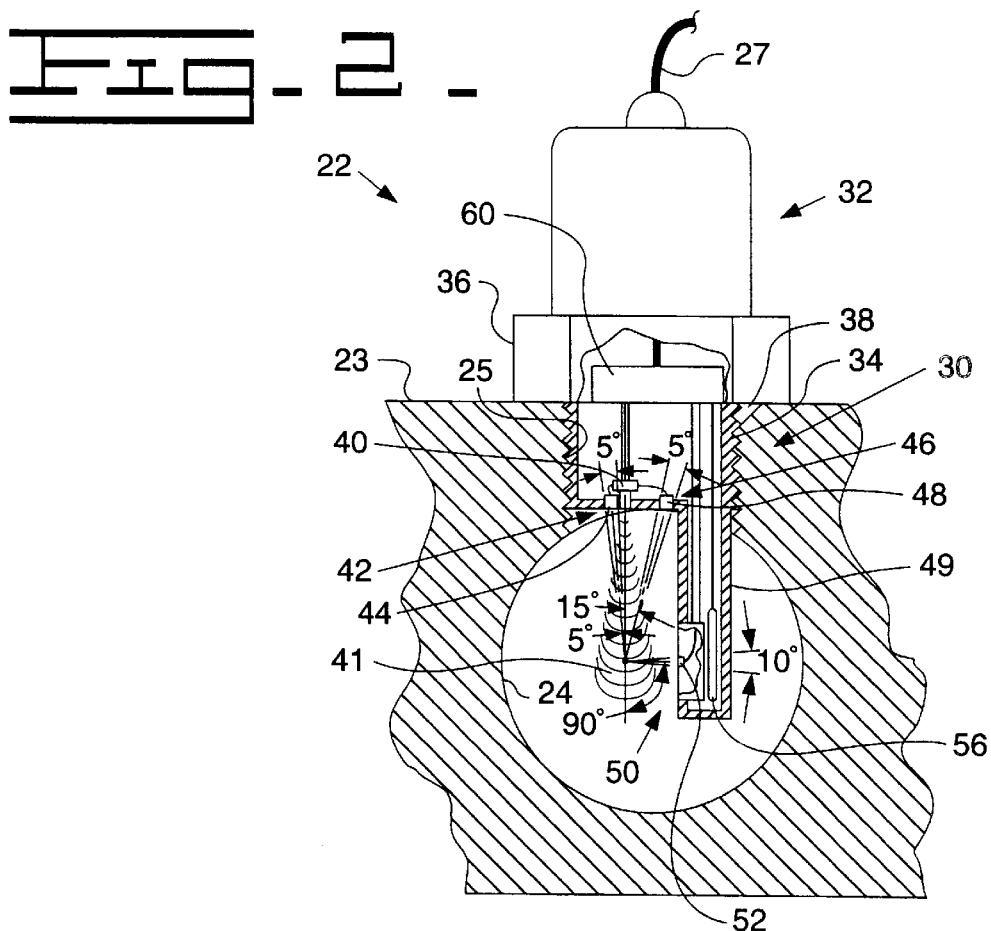
FIG. 2 is a diagrammatic representation of the subject invention disposed in the fluid system.
Figure 3:
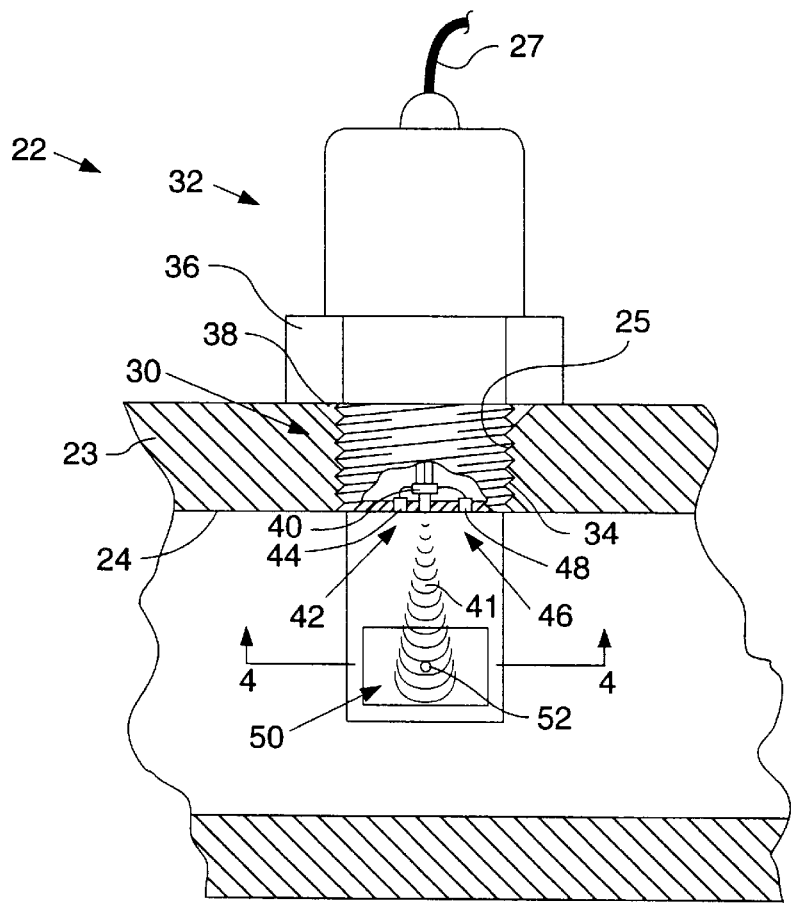
FIG. 3 is a diagrammatic representation of the subject invention disposed in the fluid system at an angle of 90 degrees to that of FIG. 2.
Figure 4:
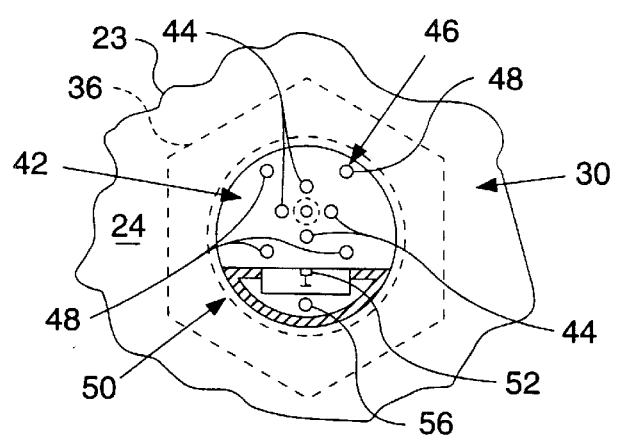
FIG. 4 is a bottom view taken from FIG. 3.

Referring to FIGS. 2, 3 and 4, the contamination sensor 22 is illustrated in greater detail. The contamination sensor 22 includes a first end portion 30, such as a sensor part, and a second end portion 32, such as a signal conditioning part. At least a portion of the first end portion has external threads 34 disposed thereon that are mateable with the threads of the threaded hole 25 defined in the sensor block 23. A hex shaped flange 36 is disposed on the second end portion 32 and operative to facilitate tightening of the contamination sensor 22 to the sensor block 23. A seal 38 is disposed between the hex shaped flange 36 and the threaded hole 35 to prevent leakage of fluid therebetween.

A source 40 of light is disposed in the first end portion 30 and is operative to direct a light beam 41 into the passage 24. As illustrated, the light beam 41 has a shape as defined by the optics of the light source 40. In the subject embodiment, the shape is in the form of a narrow, slightly diverging cone. At a predetermined distance from the source of light, the light beam 41 has a defined cross-sectional dimension. In the subject embodiment, the cross-sectional dimension is about one millimeter. The light beam 41 might be of a near infrared wavelength—in the range of 630–2000 nanometers.

A first photodetector arrangement 42 is disposed in the first end portion 30 at a location near the source 40 of light. In the subject arrangement, the first photodetector arrangement 42 includes a plurality of photodetectors 44 symmetrically centered around the source 40 of light. Each photodetector of the plurality of photodetectors 44 is spaced from the source 40 of light an equal distance.

A second photodetector arrangement 46 is disposed in the first end portion 30 at a location farther from the source 40 of light than the first photodetector arrangement 46. The second photodetector arrangement 46 includes a plurality of photodetectors 48. Each photodetector of the plurality of photodetectors 48 is spaced from the source 40 of light a second equal distance.

The first end portion 30 has an extension 49 protruding into the passage 24 parallel to the light beam 41. A third photodetector arrangement 50 is disposed in the extension 49 adjacent to and perpendicular to the axis of the light beam 41. The third photodetector arrangement 50 includes three photodetectors 52 next to each other. It is recognized that the third photodetector arrangement 50 could have more or less than three photodetectors without departing from the essence of the invention. The photodetectors 52 are located along the light beam 41 at a location where the light beam has the predefined cross-sectional dimension of about one millimeter. The photodetectors 52 of the third photodetector arrangement 50 have a collection area of about ten degrees as taken from an apex in the middle of the light beam 41 straight across from the center of the third photodetector arrangement 50. As illustrated in the drawings, the extension 49 needs to be oriented within the fluid flow so that the fluid flow passes parallel to the surface of the third photodetector arrangement 50 and is not impinged on it.

Each photodetector of the plurality of photodetectors 44 of the first photodetector arrangement 42 is spaced from the source 40 of light a distance as defined by an angle of five degrees from a line taken along the axis of the light beam 41. The apex of the angle being coincidental with the apex of the collection area for the third photodetector arrangement 50.

Each photodetector of the plurality of photodetectors 48 of the second photodetector arrangement 46 is spaced from the source 40 of light a distance as defined by an angle of fifteen degrees from a line taken along the axis of the light beam 41. The apex of the angle being coincidental with the apex of the collection area for the third photodetector arrangement 50.

Each photodetector of the first and second photodetector arrangements 42,46 has a collection area of about five degrees as taken from an apex that is common with the apex for the collection area of the third photodetector arrangement 50. It is recognized that the collection area is based on the size and shape of the respective photodetectors and could be easily varied without departing from the essence of the subject invention. It is also recognized that the quality of information received from the contamination sensor 22 is related to the area exposed to the scattered light. In order to minimize the overall size of the contamination monitor 22, the subject embodiment uses a plurality of photodetectors in each of the first and second photodetector arrangements 42,46.

A temperature sensor 56 is disposed in the projection 48 adjacent the third photodetector arrangement 50 and is operative to sense the temperature of the fluid and deliver a signal representative of the sensed temperature to the signal processing unit 26. The temperature sensor 56 may not be needed in fluid systems that are operating at a substantially constant temperature.

A signal conditioning circuit 60 is disposed in the second end portion 32. It receives the signals from the respective photodetectors and delivers electrically conditioned signals to the signal processing unit 26. The electrical signals being delivered from the signal conditioning circuit 60 of the subject embodiment is in the form of pulses and more specifically in the form of pulse width modulated signals.

The signal processing unit 26 processes the received electrical signals to determine whether the level and type of contamination in the fluid is acceptable or not. If the level and type of contamination is not acceptable, the signal processing unit directs a signal to power the bulb or light emitting diode 28 thus warning the operator that a contamination problem exists in the oil of the fluid power system 10.

It is recognized that different numbers and/or sizes of photodetectors could be used in each of the first, second and third photodetector arrangements 42,46,50 even though four is described for the first and second arrangements and three is described for the third arrangement in the subject embodiment. It is also recognized that the angular location of all of photodetector arrangements could be varied from that illustrated and described. Likewise, more than three photodetector could be used in the third photodetector arrangement 50. Additionally, the extension 49 could have various shapes. It is important to ensure that the fluid flow passing by the contamination sensor 22 is as uniform as possible.

Industrial Applicability

During operation of the fluid system 10 of the subject embodiment with the contamination sensor 22 mounted in the supply conduit 20, oil passes the respective first, second and third photodetector arrangements 42,46,50. With the light beam 41 being directed into the fluid from the source 40 of light, any contaminants, such as, solid particles, water droplets, and/or air/gas bubbles would scatter the light from the light beam 41 directed into the fluid passing through the passage 24. The contamination sensor 22 is capable of sensing contaminants within the size range from about two microns and larger. The photodetectors of the first, second and third photodetector arrangements 42,46,50 detect any light that is scattered from all types of contaminants. The magnitude and intensity of the detected scattered light from the contaminants is converted to electrical signals by the photodetectors, transferred to the signal conditioning circuit 60 and passed to the signal processing unit 26 for interpretation.

The subject invention simultaneously detects the light scattered by particles, water droplets and air/gas bubbles under a multitude of different angles. By sensing the scattered light from many different angles, different types of contaminants can be identified and their concentration can be determined since each combination of the different contaminants have reasonably unique signal responses so they can be reasonably correctly identified.

In view of the foregoing, it is readily apparent that the present invention provides a contamination sensor 22 that effectively utilizes the concept of light scatter to detect contaminants in a fluid. The structure of the contamination sensor 22 is an arrangement that is economical to produce in large quantities.

Other aspects, objects and advantages of this invention can be obtained from a study of the drawings, the disclosure and the appended claims.

I claim:

1. A contamination sensor adapted for use in a fluid system to continuously monitor the level of contaminants in the fluid, the contamination sensor comprising:

a housing having first and second end portions;

a source of light disposed in the first end portion and operative to generate a light beam therefrom;

a first photodetector arrangement disposed in the first end portion and located near the source of light;

a second photodetector arrangement disposed in the first end portion and located at a distance away from the source of light farther than the first photodetector;

a third photodetector arrangement disposed in the first end portion and located perpendicular to the light beam generated by the source of light; and a signal conditioning circuit disposed in the second end portion and operative to generate conditioned signals representative of the light intensity sensed by the respective first, second, and third photodetector arrangements.

2. The contamination sensor of claim 1 including a temperature sensor disposed in the first end portion.

3. The contamination sensor of claim 2 wherein the light beam from the source of light has an axis and is in the form of a narrow slightly diverging cone having a predetermined cross-sectional dimension at a location along its axis across from the third photodetector arrangement.

4. The contamination sensor of claim 3 wherein the predetermined cross-sectional dimension is about one millimeter.

5. The contamination sensor of claim 1 wherein the first photodetector arrangement includes a plurality of photodetectors spaced around the source of light.

6. The contamination sensor of claim 5 wherein each of the individual photodectors of the first photodetector arrangement is equally spaced from the source of light to form an angle with respect to the axis of the light beam of five degrees, the apex of the angle being within the light beam and straight across from the center of the third photodetector arrangement.

7. The contamination sensor of claim 6 wherein the second photodetector arrangement includes a plurality of photodetectors spaced around the source of light.

8. The contamination sensor of claim 7 wherein each individual photodetectors of the second photodetector arrangement is spaced equally from the source of light to form an angle with respect to the axis of the light beam of fifteen degrees, the apex of the angle being within the light beam and perpendicular to the center of the third photodetector arrangement.

9. The contamination sensor of claim 8 wherein each of the photodetectors of the first and second photodetector arrangements have a collection angle of about five degrees.

10. The contamination sensor of claim 9 wherein the third photodetector arrangement has one photodetector disposed perpendicular with the axis of the light beam and the one photodetector has a collection angle of ten degrees, the apex of the collection angle being coincident with the apices of the angles for the first and second photodetector arrangements.

11. The contamination sensor of claim 10 wherein the third photodetector arrangement has two additional photodectors disposed perpendicular to the axis of the light beam adjacent to the one photodector and the three photodectors together have a collection angle of ten degrees, the apex of the collection angle being coincident with the apices of the angles for the first and second photodector arrangements.

12. The contamination sensor of claim 11 including a temperature sensor located in the first end portion adjacent the third photodetector arrangement.

13. The contamination sensor of claim 12 wherein the wavelength of the source of light is in the range of 630 nanometers to 2000 nanometers.

14. The contamination sensor of claim 13 wherein the first end portion of the housing has external threads thereon.

* * * * *